United States Patent [19]

Hachmeister et al.

[11] 4,451,468

[45] May 29, 1984

[54] ACIDIFEROUS 17-NORMAL-PENTYL SPARTEINE TARTARIC AND FUMARIC ACID SALTS PHARMACEUTICAL COMPOSITIONS THEREOF

[75] Inventors: Bernd Hachmeister, Hanover; Wolfgang Milkowski, Burgdorf; Ulrich Kühl, Hanover; Gerd Buschmann, Hanover; Renke Budden, Hanover, all of Fed. Rep. of Germany

[73] Assignee: Kali-Chemie Pharma GmbH, Hanover, Fed. Rep. of Germany

[21] Appl. No.: 307,189

[22] Filed: Sep. 30, 1981

Related U.S. Application Data

[63] Continuation of Ser. No. 103,077, Dec. 12, 1979, abandoned.

[30] Foreign Application Priority Data

Sep. 6, 1979 [EP] European Pat. Off. ... EP 79103315.2

[51] Int. Cl.$^3$ ................. A61K 31/435; C07D 471/22
[52] U.S. Cl. ....................................... 424/256; 546/63
[58] Field of Search ................... 546/70, 63; 424/256

[56] References Cited

U.S. PATENT DOCUMENTS

| | | | |
|---|---|---|---|
| 2,946,798 | 7/1960 | Rudner | 546/63 |
| 3,755,333 | 8/1973 | Szantay et al. | 546/70 |
| 4,246,713 | 1/1981 | Montzka et al. | 546/63 |

FOREIGN PATENT DOCUMENTS

2360475  6/1975  Fed. Rep. of Germany.

Primary Examiner—Paul M. Coughlan, Jr.
Assistant Examiner—D. B. Springer
Attorney, Agent, or Firm—Schwartz, Jeffery, Schwaab, Mack, Blumenthal & Koch

[57] ABSTRACT

Acidiferous salts of 17-$\beta$-n-pentyl sparteine are crystallized out of a solution of 17-$\beta$-n-pentyl sparteine and a dicarboxylic acid selected from the group consisting of tartaric acid, fumaric acid or mixtures thereof. The novel acidiferous pentyl sparteine salts are employed in pharmaceutical compositions for the treatment of cardiac disorders and in venous therapeutical applications, and process improved stability and pharmacological properties.

7 Claims, No Drawings

ACIDIFEROUS 17-NORMAL-PENTYL SPARTEINE TARTARIC AND FUMARIC ACID SALTS PHARMACEUTICAL COMPOSITIONS THEREOF

This is a continuation of application Ser. No. 103,077, filed Dec. 12, 1979, abandoned.

BACKGROUND OF THE INVENTION

The invention concerns new pentyl sparteine salts, compositions containing the salt and a process for the preparation of such a salt and pharmaceutical composition.

The alkaloid sparteine which may be obtained from the broom plant (Cytisus scoparius) has been known for a long period of time for its favorable pharmacological properties. It is used, for example, as a venous therapeutical agent and as a cardiac medication.

The derivatives of sparteine, alkyl substituted in the 17 position of the general formula of

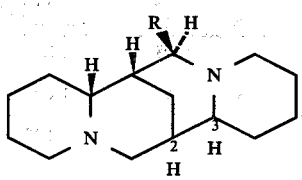

wherein R signifies an alkyl group with 1–10 carbon atoms, are pharmacologically more effective than the sparteines disclosed in West German Offenlegungsschrift No. 23 60 475 and are claimed to yield readily crystallizing salts upon conversion of the bases with conventional acids, such as hydrochloric acid, sulfuric acid, gluconic acid and perchloric acid. In the examples disclosed in West German Offenlegungsschrift No. 23 60 475, only perchlorates are isolated.

The perchlorate of 17-β-n-pentyl sparteine, a stable salt, is for a number of reasons not suitable for the preparation of drugs. One reason is that there are considerable safety risks involved in its production. For example, it is well known that alcoholic solutions containing perchloric acid are susceptible of explosions. The perchlorate salt is precipitated from an alcoholic solution. Furthermore, the perchlorate has only a 2% solubility in water at 22° C. Thus applications in the form of an aqueous solution, either by peroral or intravenous administration are essentially precluded.

There are also serious reservations against the use of the perchlorate in view of its toxicity. It is known that the substance upon application to humans may lead to leukopenia, agranulocytosis and aplastic anemia.

Attempts to obtain stable, crystalline salts with the other acids cited in West German Offenlegungsschrift No. 23 60 475, failed because only the sulfate and the hydrochloride of 17-β-n-pentyl sparteine are precipitated in the form of crystalline salts. These substances, however, are extremely hydroscopic and, therefore, are also unsuited to the preparation of medicinal drugs.

Further attempts to obtain stable salts by means of the crystallization of 17-β-n-pentyl sparteine with other acids, such as benzoic acid, acetic acid, citric acid, maleic acid, (+)camphor-10-sulfonic acid or 3-hydroxynaphthalincarbonic acid-2, have also been unsuccessful.

SUMMARY OF THE INVENTION

It is, therefore, an object of the present invention to provide a pharmacologically compatible, stable salt of 17-β-n-pentyl sparteine.

It has now been found surprisingly that the acidiferous salts of 17-β-n-pentyl sparteine with tartaric acid, fumaric acid satisfy the criteria of pharmacological compatibility and stability. These particular salts of 17-β-n-pentyl sparteine have been unkown heretofore. They may broadly be characterized as salts containing a free acid and will be referred to hereinafter as acidiferous salts or acidiferous acid addition salts.

The acidiferous acid addition salts of the present invention are defined as salts containing more than 2.1, preferably more than 2.3, molecules of acid per molecule of the base. To prepare the acidiferous salts, it is merely necessary to produce a solution containing simultaneously 17-β-n-pentyl sparteine and the salt forming acid in molar ratios of 1:1 to 1:10. The acidiferous salt precipitates in the crystalline form from the solutions and may then be dried and purified by known methods.

In a preferred embodiment, stable salts are obtained with fumaric acid, wherein the molar ratio of the base to the acid varies within the range of 1:2.5 to 1:3.0.

L(+)-tartaric acid is the particularly preferred salt forming acid. Even when the base:acid molar ratio varies between 1:1 and 1:10 in the crystallization solution, it forms an acidiferous salt with a molar composition fluctuating narrowly within a range of 1:2.5 to 1:2.8 and this ratio does not decline below the ratio of 1:2.3 even after repeated recrystallization. Salts of fumaric acid as well as mixtures of salts of tartaric and fumaric acid are also produced with these base:acid molar ratios.

The acidiferous acid addition salts have valuable pharmacological properties. As shown by the results compiled in Table 1, the acidiferous 17-β-n-pentyl sparteine-L(+) tartrate is superior to sparteine sulfate in both its pharmacological and physical properties, and comparable to pentyl sparteine diperchlorate in physical properties and superior in its pharmacological properties since pentyl sparteine diperchlorate cannot be used for pharmacological reasons.

In Table 1 in the column designated "FRP" and in the "Force" column, respectively, the concentrations ($\mu$mole/l) are given, whereby on the average the functional refractory period (FRP) is extended to 125% of the initial values and the contraction force (Force) is reduced to 75% of the initial values. These values were determined by measurements in the isolated auricle of guinea pigs by the method (modified) of Govier, as described by Govier in J. Pharmacol. exp. Ther. 148, 1000 (1965).

The $LD_{50}$, i.p. values ($\mu$mole/l) were determined by toxicity measurements on mice, eight days after a single application. The $LD_{50}$ values were calculated by the method of J. P. Litchfield et al., J. Pharmacol. exp. Ther. 96, 99 (1949).

TABLE I

|  | Acidiferous pentyl sparteine L (+)-tartrate | Pentylsparteine diperchlorate | Sparteine Sulfate |
|---|---|---|---|
| FRP | 9.1 | 7.7 | 33.9 |
| Force | 22.1 | 19.2 | 959 |
| $LD_{50}$ i.p. | 262 | 283 | 202 |

Further special advantages of the acidiferous acid addition salts consist of good stability and outstanding water solubility. Thus 17-β-n-pentyl (L+)-tartrate is soluble in water at 22° C. in a proportion of more than 100 g in 100 g water. The aqueous solutions of acidiferous acid addition salts are also characterized by good stability.

To prepare drugs containing acidiferous acid addition salts, the salts are converted into suitable galenic application forms, together with the usual carrier and/or auxiliary substance by known methods.

EXAMPLES 1 to 11

The Examples 1 to 10 demonstrate the production of acidiferous acid addition salts of the present invention, while Example 11 shows a comparative example not prepared in accordance with the invention.

These examples are summarized in Table II.

dried ether products are distilled off. An oily residue soluble in alcohol is left. By the addition of perchloric acid to achieve an acid reaction the 17-isobutylspartein diperchlorate is caused to crystallize out.

Yield: 11.1 g (57%). Melting Point: 272°–274° C.

The 17-hydroxy sparteine required was prepared by the process of West German patent application No. P 28 25 117. Additional pertinent portions of West German application Nos. 28 25 117 and 23 60 475 are incorporated herein by reference.

The acidiferous acid addition salts prepared in Examples 1 to 10 and their 1% aqueous solutions exhibit good stability. In stability tests, no dissociation was found in thin layer chromatographic investigations. One test included storage for one month at 55° C. and as a second test utilized exposure to light (30 hours, rapid light exposure instrument "SUNTEST," Heraeus Co.).

Examples 12 to 14 show galenic preparations using

TABLE II

PREPARATION OF ACIDIFEROUS ACID ADDITION SALTS

| Example | Type of Acid | Amount of Base (g) | Amount of Acid (g) | Mole Ratio of Reaction Mixture (base:acid) | Solvent X Y ml | Yield (g) | Salt (%) | Molar Ratio of Salt (base:salt) | Melting Point (C.°) |
|---|---|---|---|---|---|---|---|---|---|
| 1 | L(+)-tartaric acid | 9.13 | 11.5 | 1:2.55 | Ethanol 30 50 | 19.9 | 98 | 1:2.55 | 176–178 |
| 2 | L(+)-tartaric acid | 9.13 | 13.5 | 1:3 | Ethanol 100 100 | 19.3 | 90 | 1:2.74 | |
| 3 | L(+)-tartaric acid | | Nr.2 | Three times recrystallized from Ethanol | | | | 1:2.37 | |
| 4 | L(+)-tartaric acid | 1.7 | 4.2 | 1:5 | Ethanol 20 20 | 3.8 | 94.6 | 1:2.76 | 177 |
| 5 | L(+)-tartaric acid | 1.7 | 8.4 | 1:10 | Ethanol 20 40 | 3.0 | 78.9 | 1:2.51 | 180 |
| 6 | (L+)-tartaric acid | 1.52 | 1.5 | 1:2 | Isopropanol 20 20 | 2.2 | 79 | 1:2.52 | |
| 7 | L(+)-tartaric acid | 1.52 | 1.5 | 1:2 | Acetone 20 20 | 2.1 | 76 | 1:2.5 | |
| 8 | D(−)-tartaric acid | 3.05 | 3 | 1:2 | Ethanol 30 30 | 5.05 | 75 | 1:2.46 | |
| 9 | Fumaric acid | 3.05 | 2.32 | 1:2 | Ethanol 30 30 | 4.38 | 73 | 1:2.55 | 145 |
| 10 | Fumaric acid | 3.05 | 2.32 | 1:2 | Ethanol 30 30 | 4.03 | 62 | 1:2.98 | |
| 11 | Sulfuric acid | 3.05 | 1.96 | 1:2 | Ethanol 30 8 | Smeary crystals were obtained which very rapidly dissolved during suctioning by absorbing atmospheric humidity. | | | |

According to the data in Table II, 17-β-n-pentyl sparteine is dissolved in X ml of the hot solvent. To this solution is added a hot solution of the acid to Y ml of the hot solvent. The white precipitate crystallizing after cooling is suctioned off, washed with a small quantity of the cold solvent and dried in vacuo at 120° C.

To determine the composition of the salt, the 17-β-n-pentyl sparteine base content is determined titrametrically with perchloric acid in glacial acetic acid/acetanhydride. The acid was titrated in water/isopropanol with sodium hydroxide.

In the preparation of 17-β-n-pentyl sparteine the procedure of West German Offenlegungsschrift No. 23 60 475 was followed. More particularly, to a solution of 16.4 g isobutylbromide in 40 ml absolute ether are added 3.2 g magnesium chips. The mixture is further diluted with 40 ml ether. The Grignard compounds are formed and heated gently to achieve full substitution upon completion of the reaction. Next, 10 g 17-hydroxyspartein in 20 ml absolute ether are added dropwise to the solution. The mixture is heated for one hour in a water bath after which water is added and the ether phase is separated. A subsequent separation of water and ether phase is thereafter conducted. The combined the 17-β-n-pentyl sparteine from Experiment 1. The "parts" terminology signifies "parts by weight" in all of the examples.

EXAMPLE 12

TABLETS

Ingredients:

| 17-β-n-pentyl sparteine-L(+)-tartrate | 75 parts |
|---|---|
| Lactose | 250 parts |
| Corn starch | 160 parts |
| Soluble starch | 10 parts |
| Magnesium stearate | 5 parts |
| Total | 500 parts |

Prescription:

17-β-n-pentyl sparteine-L(+)-tartrate, lactose and the corn starch are thoroughly mixed in a LODIGE mixer and then granulated with a 20% aqueous solution of the soluble starch. The humid mass is passed through a 1.6 mm sieve and subsequently dried in a fluidized bed dryer with the inlet air at 70° C. to a water content of approximately 4%. The granulate obtained in this manner is passed through a 1 mm sieve, mixed with magnesium stearate and pressed into tablets with diameters of 12 mm. The weight of each tablet is 500 mg on the average, so that a single dose always contains 75 mg of the active ingredient.

Example 13

TABLETS, RETARDATION FORM
Ingredients:

| | |
|---|---|
| 17-β-n-pentyl sparteine-L(+)tartrate | 300 parts |
| Aerosil | 5 parts |
| Hydrated castor oil | 100 parts |
| Methylhydroxypropylcellulose | 50 parts |
| Talc | 45 parts |
| Total | 500 parts |

Prescription:

17-β-n-pentyl sparteine-L(+)-tartrate, hydrated castor oil, Aerosil and talc are thoroughly mixed in a LODIGE mixer and granulated with a solution of methylhydroxypropylcellulose in a mixture of methylene chloride/ethanol (60:40). The humid mass is passed through a 1.6 mm sieve and dried on a screen overnight at 40° C. The dry product is again passed through a 1.6 mm sieve and pressed into corners of 11 mm diameter. The weight of each core is 500 mg on the average, so that a single dose always contains 300 mg of the active ingredient.

The cores are subsequently provided with a coating of commercially available Eudragit RS (10 mg per core) by a known process. (Endragit RS is a copolymer of the ROHM Co., consisting of trimethylammoniumethylmethacrylate chloride, methacrylic acid methylester and acrylic acid ethyl ester in a ratio of 5:65:30).

EXAMPLE 14

AMPOULES

| | |
|---|---|
| 17-β-n-pentyl sparteine-L(+)-tartrate | 75 parts |
| Sodium chloride | 9 parts |
| Water | 916 parts |
| Total | 1000 parts |

Prescription:

17-β-n-pentyl sparteine-L(+)-tartrate and sodium chloride are dissolved in water, the solution filtered and sterilized after filling in 1 ml ampoule bottles. Each ampoule contains 75 mg of the active ingredient.

What is claimed is:

1. An acidiferous acid addition salt of 17-β-n-pentyl sparteine of the following formula:

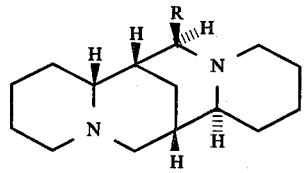

wherein R is n-pentyl and a dicarboxylic acid selected from the group consisting of tartaric acid, and fumaric acid wherein the ratio of moles of acid to moles of base in said salt is between 2.1 and 3.5 moles of acid for each mole of base.

2. The acidiferous acid addition salt of claim 1 wherein the dicarboxylic acid is L(+)-tartaric acid.

3. The acidiferous acid addition salt of claim 1 or 2 wherein the ratio is between 2.3:1 and 3.0:1.

4. The acidiferous acid addition salt of claim 2 wherein the ratio of moles of acid to moles of base in said salt is between 2.5 and 2.8 moles of acid for each mole of base.

5. A stable, pharmacologically active 17-β-n-pentyl sparteine composition useful in the treating of cardiac rhythm disorders comprising a pharmacologically acceptable carrier and a pharmaceutically effective amount of the acidiferous acid addition salt of 17-β-n-pentyl sparteine of the following formula:

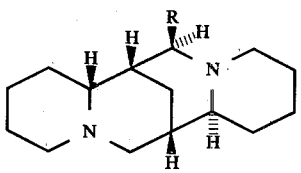

wherein R is n-pentyl and a dicarboxylic acid selected from the group consisting of tartaric acid, and fumaric acid wherein the ratio of moles of acid to moles of base in said salt is between 2.1 and 3.5 moles of acid for each mole of base.

6. The stable, pharmacologically active 17-β-n-pentyl sparteine of claim 5 wherein the dicarboxylic acid is L(+)-tartaric acid.

7. The stable, pharmacologically active 17-β-n-pentyl sparteine of claim 5 or 6 wherein the ratio of moles of acid to moles of base is between 2.3 and 3.5 for each mole of base.

* * * * *